(12) United States Patent
Kane et al.

(10) Patent No.: US 7,008,803 B2
(45) Date of Patent: Mar. 7, 2006

(54) METHOD OF REWORKING STRUCTURES INCORPORATING LOW-K DIELECTRIC MATERIALS

(75) Inventors: Terence Lawrence Kane, Wappingers Falls, NY (US); Chung-Ping Eng, Hopewell Junction, NY (US); Brett H. Engel, Wappingers Falls, NY (US); Barry Jack Ginsberg, Poughkeepsie, NY (US); Dermott A. Macpherson, Pleasant Valley, NY (US); John Charles Petrus, Lagrangeville, NY (US)

(73) Assignee: International Business Machines Corporation, Armonk, NY (US)

( * ) Notice: Subject to any disclaimer, the term of this patent is extended or adjusted under 35 U.S.C. 154(b) by 295 days.

(21) Appl. No.: 10/280,513

(22) Filed: Oct. 24, 2002

(65) Prior Publication Data

US 2004/0082176 A1 Apr. 29, 2004

(51) Int. Cl.
*H01L 21/00* (2006.01)
(52) U.S. Cl. .......................... 438/7; 438/723; 450/489
(58) Field of Classification Search ................ 438/706, 438/710, 714, 719, 720, 723, 724, 725, 6, 438/7; 250/489
See application file for complete search history.

(56) References Cited

U.S. PATENT DOCUMENTS

| 4,874,947 | A | * | 10/1989 | Ward et al. ................. 250/309 |
| 5,948,217 | A | * | 9/1999 | Winer et al. ........... 204/192.34 |
| 6,180,976 | B1 | * | 1/2001 | Roy ........................... 257/306 |
| 6,281,025 | B1 | * | 8/2001 | Ring et al. .................... 438/10 |
| 6,565,720 | B1 | * | 5/2003 | Ring ..................... 204/192.34 |
| 6,630,395 | B1 | | 10/2003 | Kane et al. |
| 6,746,961 | B1 | * | 6/2004 | Ni et al. ..................... 438/700 |

* cited by examiner

*Primary Examiner*—Kin-Chan Chen
(74) *Attorney, Agent, or Firm*—Lisa J. Ulrich

(57) ABSTRACT

Methods of etching a semiconductor structure using ion milling with a variable-position endpoint detector to unlayer multiple interconnect layers, including low-k dielectric films. The ion milling process is controlled for each material type to maintain a planar surface with minimal damage to the exposed materials. In so doing, an ion beam mills a first layer and detects an endpoint thereof using an optical detector positioned within the ion beam adjacent the first layer to expose a second layer of low-k dielectric film. Once the low-k dielectric film is exposed, a portion of the low-k dielectric film may be removed to provide spaces therein, which are backfilled with a material and polished to remove the backfill material and a layer of the multiple interconnect metal layers. Still further, the exposed low-k dielectric film may then be removed, and the exposed metal vias polished.

8 Claims, 7 Drawing Sheets

METHOD OF REWORKING STRUCTURES INCORPORATING LOW-K DIELECTRIC MATERIALS

FIELD OF THE INVENTION

Figure 1:
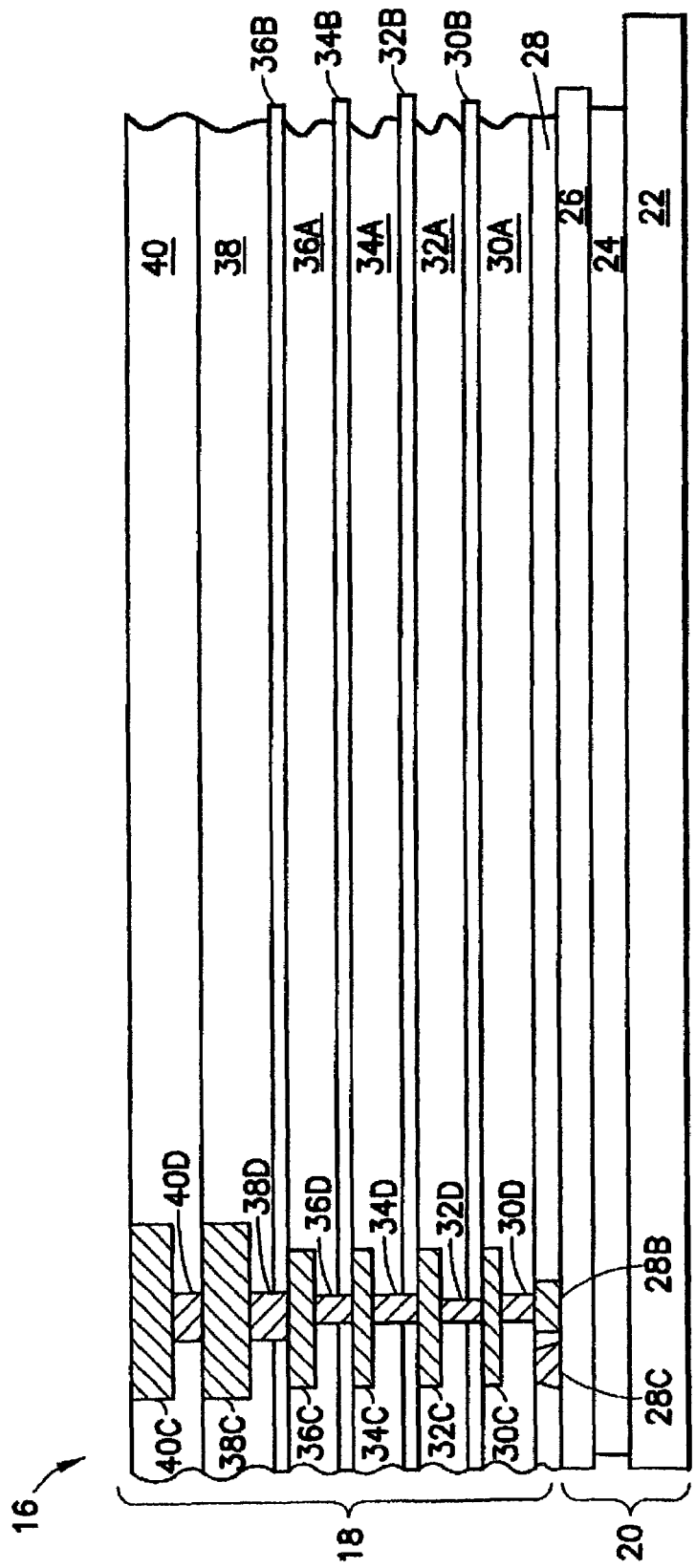

The present invention relates to methods and systems for unlayering multi-layer structures incorporating low-k dielectric materials.

BACKGROUND OF THE INVENTION

Advanced semiconductor designs typically incorporate planarized multilevel structures including alternating layers of insulating materials supporting dual damascene and single damascene metal interconnections. Exemplary structures include alternating layers of insulating films, for example low-k dielectric films, with alternating chemical-mechanical hardmask endstop layers, for example silicon nitride and/or high density plasma oxide. Damascene metal can comprise, for example, copper.

Selective unlayering of these multilayer structures is often necessary for purposes of manufacturing rework or recovery of wafers, to perform defect yield analysis, and/or for electrical characterization or physical failure analysis of wafers, wafer fragments, individual dies, or packaged dies to perform reliability defect root cause analysis. Regular unlayering of these multi-layer structures can also be done in the course of automated pattern recognition inspection of defects in comparison with electrical test maps.

Unlayering multi-layer structures including low-k dielectric materials is problematic using known layer removal techniques. In particular, the fragile nature of the low-k dielectric materials cause them to react poorly to processes effective for oxides. For example, the lower modulus of low-k dielectric films are susceptible to damage when exposed to conventional chemical-mechanical polish processes. Wafer delayering for manufacturing rework or recovery of wafers cannot employ conventional delayering processes using plasma, or reactive ion etching or chemical-mechanical polish removal for planar deprocessing low-k films without damaging underlying films and undercutting metal layers. Still other techniques involving incident gallium ion beams can result in undesirable implantation of gallium into the low-k films or produce beam interactions (i.e. chemical bond breakdown in organic components present in some low-k films) producing unwanted electrical leakage paths and electrical shorts.

Further, conventional processes used to remove overlying metal layers, particularly copper single damascene and copper dual damascene metal, can result in damage to the underlying low-k dielectric layers. For example, conventional chemical-mechanical removal of copper layers can easily scratch, or embed polishing media or slurry into, underlying low-k films, by compromising hardmask endstop materials. Attempts to unlayer multilevel structures using conventional reactive ion etching can produce non-planar etch results due to the presence of porous regions within the low-k film as well as the in-homogenity of the low-k films, themselves.

Conventional reactive ion etching of copper requires elevated temperatures, producing nonvolatile species that can contaminate low-k dielectric films. Further, reactive ion etch removal of overlying insulating films can result in undercutting of underlying copper metal layers resulting in non-uniform etch removal of underlying low-k dielectric films.

New and improved processes are thus desirable which facilitate the selective planar de-processing of metal layers, hardmask materials and chemical-mechanical endstop materials over low-k dielectric films without damaging the underlying low-k dielectric layers.

SUMMARY OF THE INVENTION

Two proposed methods involving deprocessing low-k structures with copper metallurgy/copper interconnections are described.

First, a new and improved apparatus and methods involving collimated Argon ion beam milling/Chemical assisted Argon Ion beam etching is provided for unlayering multi-layer structures including low-k dielectric layers with minimal damage to the low-k dielectric films while maintaining planarity of the unlayered surface. Such methods and apparatus are applicable, for example, to unlayering back-end multilevel metallurgy found in semiconductor devices.

In accordance with one embodiment of the invention, there is provided a method of ion beam etching a semiconductor structure including a first layer of material overlaying a second layer of low-k dielectric film, comprising the steps of: ion beam-milling the first layer of material; and detecting, with an optical detector positioned in the ion beam adjacent the first layer of material, an endpoint of the first layer; whereby to expose the second layer of low-k dielectric film.

In another embodiment of the invention, there is provided a system for delayering a semiconductor structure including a first layer of material overlaying a second layer of low-k dielectric film, comprising: a processing chamber; an ion beam milling source in the processing chamber for generating a beam of ions to mill the semiconductor structure; a platen in the processing chamber for supporting the semiconductor structure in the beam of ions; a sapphire crystal endpoint detector in the processing chamber; a photospectrometer outside of the processing chamber; means for connecting the sapphire crystal endpoint detector to the photospectrometer; and means for positioning the sapphire crystal endpoint detector proximate the platen to monitor milling of the semiconductor structure.

Secondly, a set of processes for deprocessing spun-on low-k structures with copper metallurgy/copper interconnections is described.

DESCRIPTION OF THE DRAWING FIGURES

These and other objects, features and advantages of the invention will be apparent from a consideration of the Detailed Description of the Invention when read with consideration of the drawing Figures, in which:

FIG. 1 is a cross-sectional view of a semiconductor device including a back-end, multilevel metal contact structure exemplary of one type to which the invention is applicable; and FIGS. 2–7 are cross-sectional views of the multilevel metal contact structure of FIG. 1 showing successive processing steps in accordance with one embodiment of the invention.

DETAILED DESCRIPTION OF THE INVENTION

Methodology for Reworking/Recovering Whole Wafers/Wafer Fragments/Individual Die:

With reference now to FIG. 1, there is shown a semiconductor structure 16 including a silicon device front-end 20 overlain by a multilevel metal back-end structure 18. Front end 20 comprises a conventional silicon-on-insulator (SOI) construction including a device-bearing, doped semiconductor layer 26 overlying an insulator layer 24 over a single-crystal silicon layer 22. Semiconductor devices formed by implantation and processing in layer 26 are contacted through back-end structure 18 in the manner described below.

Continuing with reference to FIG. 1, back-end structure 18 is seen to comprise a first-level connector layer including an insulator layer 28A, such as an oxide, having a metal-filled via 28B for contacting semiconductor devices on doped silicon layer 26. Metal-filled via 28B contacts a source/drain region on the surface of doped silicon layer 26 adjoining a gate structure 28C of a semiconductor field-effect transistor (FET). If the gate material is silicon oxide, this device is further identified as a metal-oxide FET, or MOSFET.

A series of four layers of a low-k dielectric material, indicated at 30A, 32A, 34A and 36A, respectively, overlay layer 28A, each low-k layer in turn overlain by an insulator layer 30B, 32B, 34B and 36B. Insulator layers 30B–36B each comprises a hardmask, chemical-mechanical endstop, such as a nitride, which will be used, in a manner described below, as an etching mask in a process for exposing the underlying low-k dielectric layer. Each series of low-k film/insulator layers 30A/B–36A/B includes a metal-filled via interconnect extending there through, the metal-filled vias indicated respectively at 30D, 32D, 34D and 36D. A series of metal connector layers, indicated respectively at 30C, 32C, 34C and 36C, are interposed between adjacent vias.

Two oxide layers, indicated respectively at 38 and 40, overlie insulator layer 36, each oxide layer including a metal-filled via 38D, 40D and overlying metal layer 38C, 40C. A respective silicon nitride chemical-mechanical etch stop layer, 38A, 40A, overlies each oxide layer 38, 40.

It will be appreciated that back-end structure 18 illustrates a conventional multilevel metal structure with a first interconnect 28B, for example comprising tungsten, overlaid by six, and optionally more, levels of metal vias and connectors graphically represented by 30C/D, 32C/D, 34C/D, 36C/D, 38C/D and 40C/D. Typically, these metal interconnections comprise dual damascene copper and single damascene copper. In the described embodiment of the invention, the tungsten metal wiring level identified as 28B combined with the successive overlying copper metal lands identified as 30C, 32C, 34C, 36C, 38C and 40C would comprise what is known in the art as 'seven level metal.' Various methods and materials are known in the art for fabricating this type of structure.

As described above, low-k dielectric layers are identified at 30A–36A. Typically, these low-k dielectric layers comprise materials having a k factor of about 2.85 or less. Such films typically comprise PECVD-deposited SiCOH films and compounds thereof, PECVD-deposited carbon-doped oxides and other organic polymers and porous oxides. Commercially available low-k dielectric products and materials include Dow Corning's SiLK™ and porous SiLK™, Applied Materials' Black Diamond™ Novellus' Coral™, Honeywell's HOSP™, and Trikon Technologies FLOW-FILL™, among others.

Low-k dielectric films have desirable electrical characteristics effective to significantly reduce the lateral and inter-level capacitive effects between closely spaced electrical conductors of multilevel metal. Such conductors include, for example, the dual damascene-formed copper conductors described above.

As noted above, however, these low-k dielectric materials possess certain chemical and mechanical characteristics that make them prone to damage from certain common semiconductor processes. They are, for example, soft, pliable and porous as well as susceptible to damage through the use of typical semiconductor processes. Processes typically used to remove or unlayer low-k dielectric materials, such as mechanical unlayering, reactive ion etching (RIE), focused ion beam (FIB) techniques, chemical-mechanical polishing and wet chemical removal processes may damage the low-k or cause conductive leakage paths within the dielectric layers themselves.

It will be understood that the terms "layer" and "film," and variants thereof, are used interchangeably herein to describe the thin, conformal sheets of semiconductor, insulator and conductive materials that comprise a semiconductor device structure. It will be further understood that the terms "low-k dielectric material" and "SiLK," and variants thereof, are used interchangeably herein to described the low-k dielectric materials described above.

Figure 2:
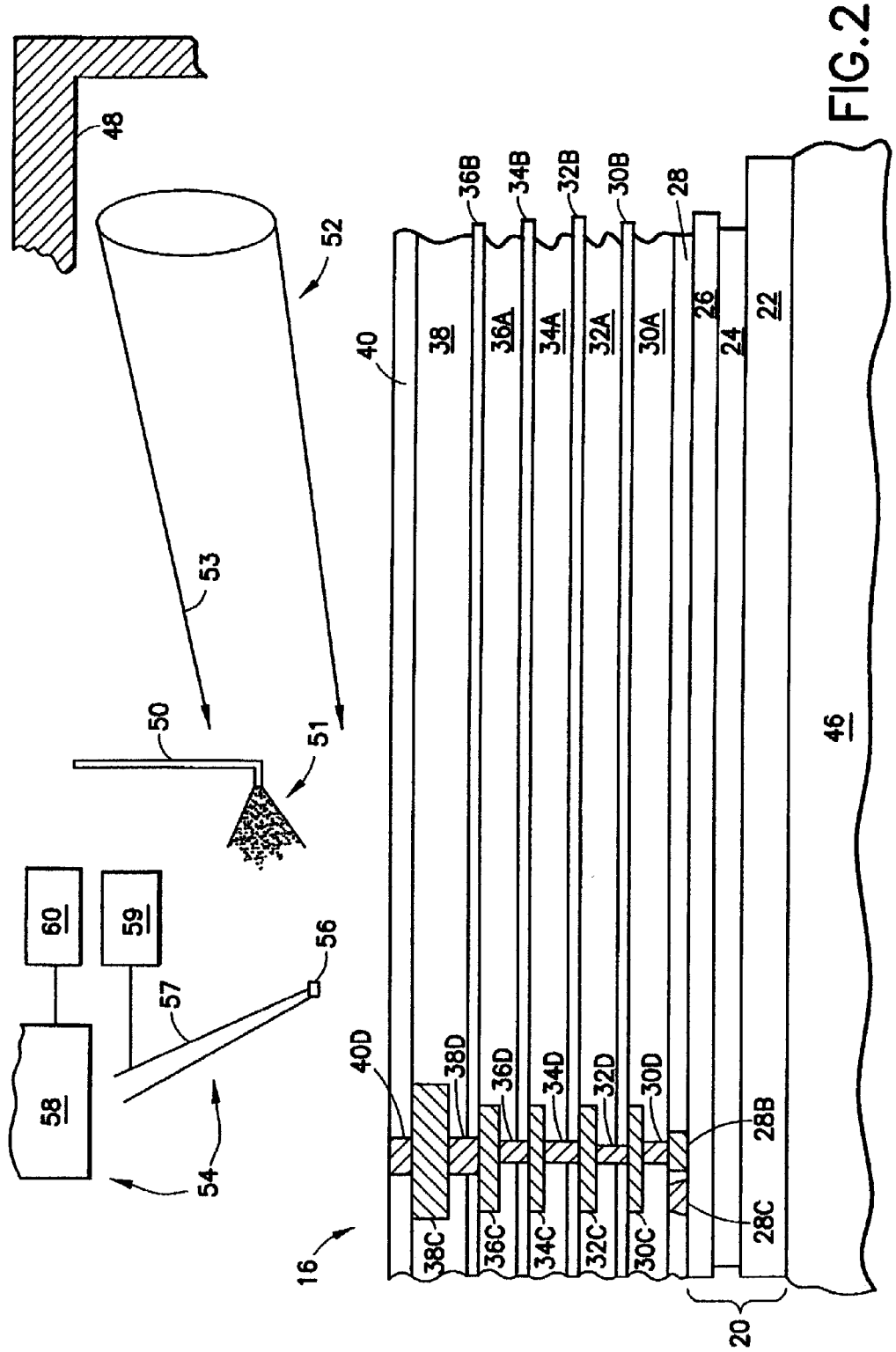

With reference now to FIG. 2, there is shown semiconductor structure 16 having hardstop layer 40A and oxide layer 40 removed down to via 40D. Partial oxide layer 40 may be removed using one of many known processes including, for example, chemical-mechanical polishing or reactive ion etching.

As further shown in FIG. 2, structure 16 is situated in a processing chamber 48, comprising, for example, one of many commercially known vacuum chambers available with a vacuum feedthrough and a tungsten filament ion beam source or a filament-less source. Processing chamber 48 supports structure 16 on a liquid-cooled platen 46 capable of full rotation and full tilt and of cooling in a range of −15 to +35 degrees centigrade.

In the described embodiment, a cooling media of 50% di-ionized water and 50% ethylene glycol-antifreeze is used to control the temperature of structure 16, preventing damaging overheating from incident ion beam energy by heat exchange cooling of platen 46. Structure 16 is attached to platen 46, for example, using heat dissipating grease. Alternatively, a cooling helium gas can be metered into a fixture (not shown) holding structure 16 for incident ion beam delayering. Processing chamber 48 accommodates a line 50 for introducing a focused input of a controlled mixture of a selected processing gas(es) 51 into the chamber. Processing chamber 48 further supports an argon ion beam milling source 52.

In the described embodiment, ion beam milling source 52 is manufactured by milling tool manufacturer VEECO instruments. The system has been modified with the addition of a gas nozzle for introducing gases into the chamber. Further included are four individual mass flow controllers for metering separate gases controlled via an external computer (not shown) having a conventional RS232 interface to monitor gas flow rates.

In the described embodiment, milling source 52 comprises a 400 watt pulse-mode 30 kHz switchable DC power supply, avoiding the risk of charge-inducted damage that may be associated with conventional 13.56 mHZ RF generators typically used in RIE/PLASMA etching systems. Milling source 52 preferably includes a circumferential charge neutralizing filament 53 surrounding the collimated Argon beam. Milling source 52 is capable of currents in the range of 300 eV-3 KeV for a full range of incident beam energies.

While the invention is described with respect to Argon ion beam milling, any inert noble gas species found in the same column of the periodic table as Argon, including helium, neon, xenon, and radon would work. Noble gases ionize in a plasma to form non reactive, inert ions. Argon gas is typically selected for all plasma processes because it is inexpensive and requires the least energy to disassociate into ions and form a plasma.

Processing chamber 48 further includes a fiber optic photospectrometer endpoint detector system 54. Endpoint detector system 54 includes a sapphire tip detector 56 positioned within the argon ion beam near the region of interest on semiconductor structure 16. Sapphire tip detector 56 is connected, through a ferro-fluidic vacuum feed-through accommodating a stainless steel tube housing an appropriate fiber optic cable, the tube and cable assembly indicated at 57, to a personal-computer based charge-coupled device (CCD) CCD LV-VIS array spectrophotometer 58 located outside of chamber 48. In the described embodiment, a standard PCI card is used for interfacing spectrophotometer 58 with a computer (PC) 60. The tube/cable 57 is preferably motor operated in a conventional manner by an electromechanical positioning device 59 so that detector 56 can be repositioned at various process steps to be proximate regions of interest on semiconductor substrate 16.

In a manner known in the art, spectrophotometer 58 can be tuned to various peak sensitivities, including copper peak sensitivity, tantalum liner peak sensitivity, carbon peak sensitivity (for such organic low-k dielectric films as SiLK), silicon peak sensitivity (for PECVD silicon oxide and LPCVD/HDP silicon nitride dielectrics), as well as tungsten peak sensitivity for tungsten interconnection, to detect different types of endpoint materials. This spectrophotometer may, for example, be controlled using PC 60 running Visual C++ software code.

As is further described below, the above-described equipment is used in an argon ion beam milling process to etch back end structure 18, including the various insulator, metal and low-k dielectric film layers. It will be seen that the etching process results in highly controllable, essentially planar delayering, while avoiding the damage to low-k materials typically associated with prior art processes, including: damage caused by FIB gallium beam induced charge implantation, undesirable anisotropic etch profiles associated with reactive ion etching (RIE) etch profiles, oxygen and H2O uptake in SiLK low-k films, solvent uptake in low-k dielectric films as well as susceptibility to scratching/slurry particle embodiment damage by chemical-mechanical processing.

Applicant has developed the following, exemplary operating parameters for planarizing low-k dielectric films:

For planarizing Dow Corning Porous SiLK (porous methyl silsequioxane; k=2.2)
- Argon ion beam currents in the range of 100 mA/cm$^2$ to 150 mA/cm$^2$ (maximum of 300 mA/cm$^2$)
- Accelerating voltages in the range of 300 eV to 400 eV (maximum of 650 eV)
- Angle of Incidence of Argon Beam to stage/sample surface in the range of 7 degrees up to 21 degrees (93 degrees from normal to 79 degrees from normal);
- Chuck temperature control in the range of 0 degrees centigrade to 15 degrees centigrade (maximum)
- Heat transfer/heat conduction to liquid cooled chuck; Silicone based grease such as MUX for minimum out-gassing and greatest heat dissipation
- Stage rotation: about 10 rpm
- Charge Neutralizing Current: about 300 uA (maximum)
- Argon Magnet Voltage Level: in the range of about 0.80 mV to 0.85 m Volts These parameters will result in an etch rate in the range of 250 A/minute to 440 A/minute, depending on incident angle and beam current.

For planarizing Dow Corning SiLK (k=2.65)
- Beam Currents in the range of 150 mA/cm$^2$ to 250 mA/cm cm$^2$
- Accelerating voltages in the range of 400 eV to 500 eV (maximum of 650 eV)
- Angle of Incidence of Argon Beam to stage/sample surface in the range of 7 degrees up to 21 degrees (93 degrees from normal to 79 degrees from normal);
- Chuck temperature control in the range of 0 degrees centigrade to 15 degrees centigrade (maximum)
- Heat transfer/heat conduction to liquid cooled chuck; Silicone based grease such as MUX for minimum out-gassing and greatest heat dissipation
- Stage rotation; about 10 rpm
- Charge Neutralizing Current: about 300 uA (maximum)
- Argon Magnet Voltage Level; in the range of about 0.80 to 0.85 mV These parameters will result in an etch rate in the range of 225 A/minute to 400 A/minute, depending on incident angle and beam current.

Still with reference to FIG. 2, assembly 57 is used to position sapphire detector 56 proximate the upper surface of remaining oxide layer 38. Spectrophotometer 58 is adjusted to sense nitride, by optimizing the signal to detect silicon nitride. A selected gas 51, for example a mixture of CF4 and oxygen, is introduced into chamber 48 and the parameters of ion beam milling source 52 and platen 46 are adjusted in a conventional manner to optimize the etching of oxide and copper. The mixture of CF4 gas and oxygen will preferentially etch oxide and nitride without attacking copper. Ion beam milling would mill copper at one rate while ionized gas would preferentially etch oxide and nitride. Milling source 52 is operated to remove the remaining portion of oxide layer 40 along with the copper in copper-filled via 40. When photospectrometer 58 detects nitride from nitride layer 38, the process is terminated.

Figure 3:
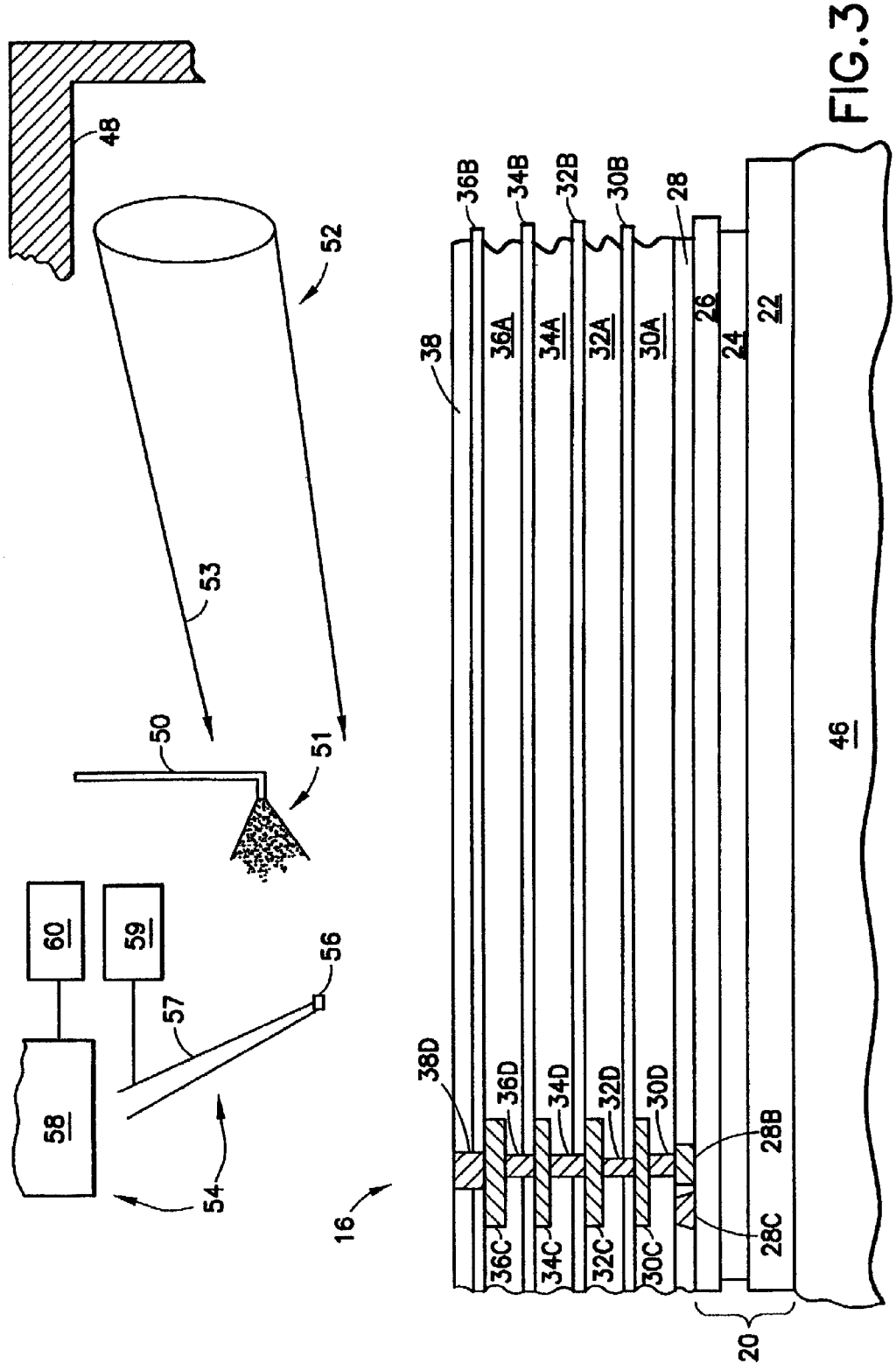

With reference now to FIG. 3, photospectrometer 58 is adjusted to sense oxide by optimizing the signal to sense oxygen or silicon but NOT nitride, and the parameters of gas 51, milling source 52 and platen 46 are optimized in a conventional manner to etch nitride and copper. Nitride layer 38A is thus removed along with copper conductor 38C, exposing the upper surface of remaining oxide layer 38 and copper filled via 38D as shown in FIG. 3.

It will be understood that following each etching step, assembly 54 and platen 46 are manipulated to place semiconductor structure 16 and endpoint detector 56 in the optimum physical position for the next etch step. Endpoint detector 56 can be placed directly within the ion beam of milling source 52 proximate the areas of interest being etched. The temperature, angle and position of platen 46 are adjusted to optimize the etch process for the materials being etched.

Figure 4:
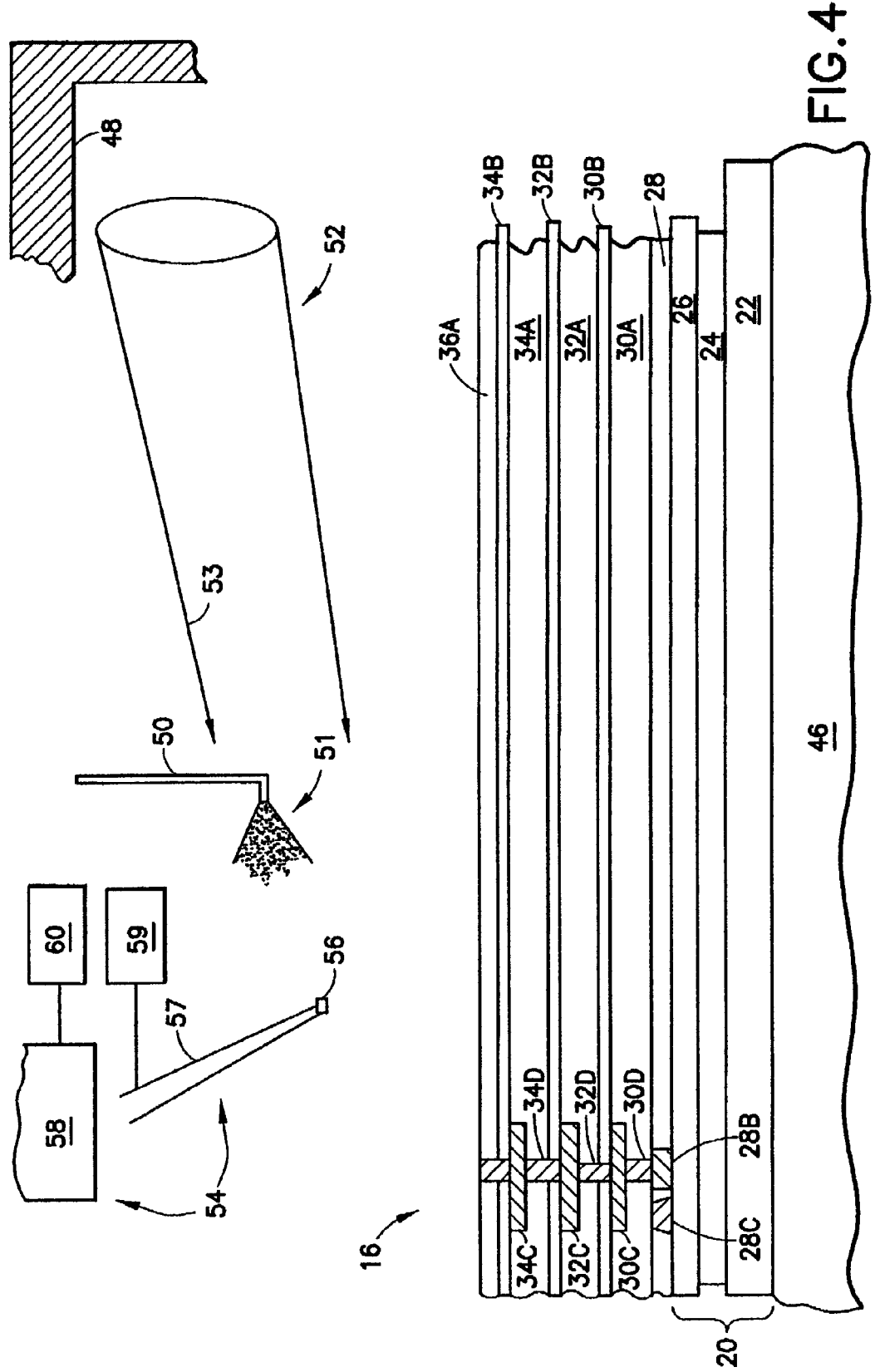

With reference now to FIG. 4, photospectrometer 58 is adjusted to sense a low-k dielectric film such as SiLK by optimizing for sensing a carbon peak, the principal elemental component of an organic low-k film. By sensing the appropriate principal elemental component, i.e. for conventional oxides, this would be oxygen or silicon; for silicon nitride, this would be nitrogen, the above-described etching processes are used to remove the remaining portion of oxide layer 38, nitride layer 36 and the copper connectors and copper-filled vias there through, exposing low-k dielectric layer 36A and copper-filled via 36D as shown in FIG. 4.

It will be appreciated from a consideration of the process description and drawings that the etching systems and processes that are the subject of the present invention yield highly planar exposed surfaces, regardless of the materials being etched. Further, the processes can be controlled to accurately etch very thin films and very small depths within films, thus enabling the exposure of substantially any desired layers or features within a semiconductor structure.

Figure 5:
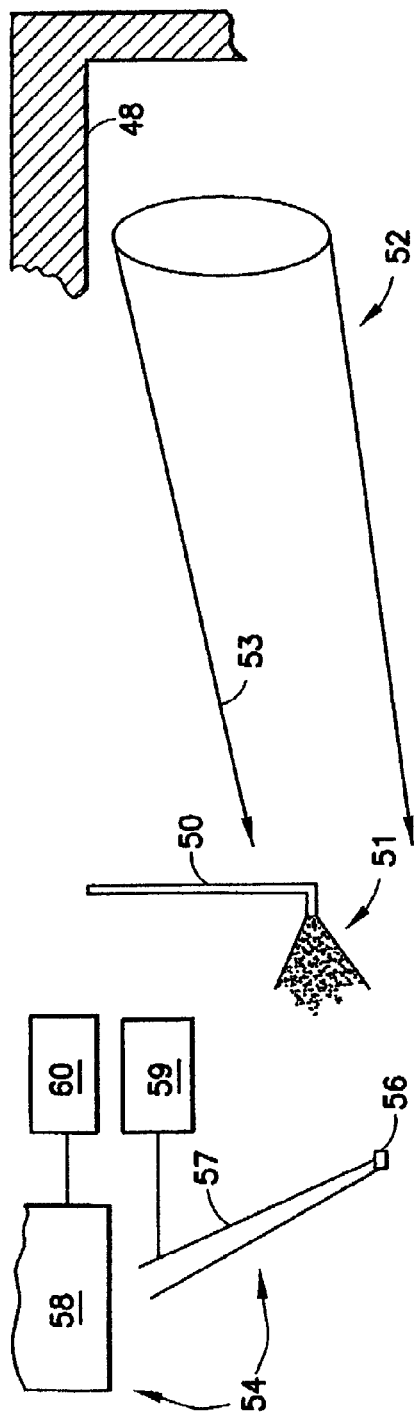
Figure 5:
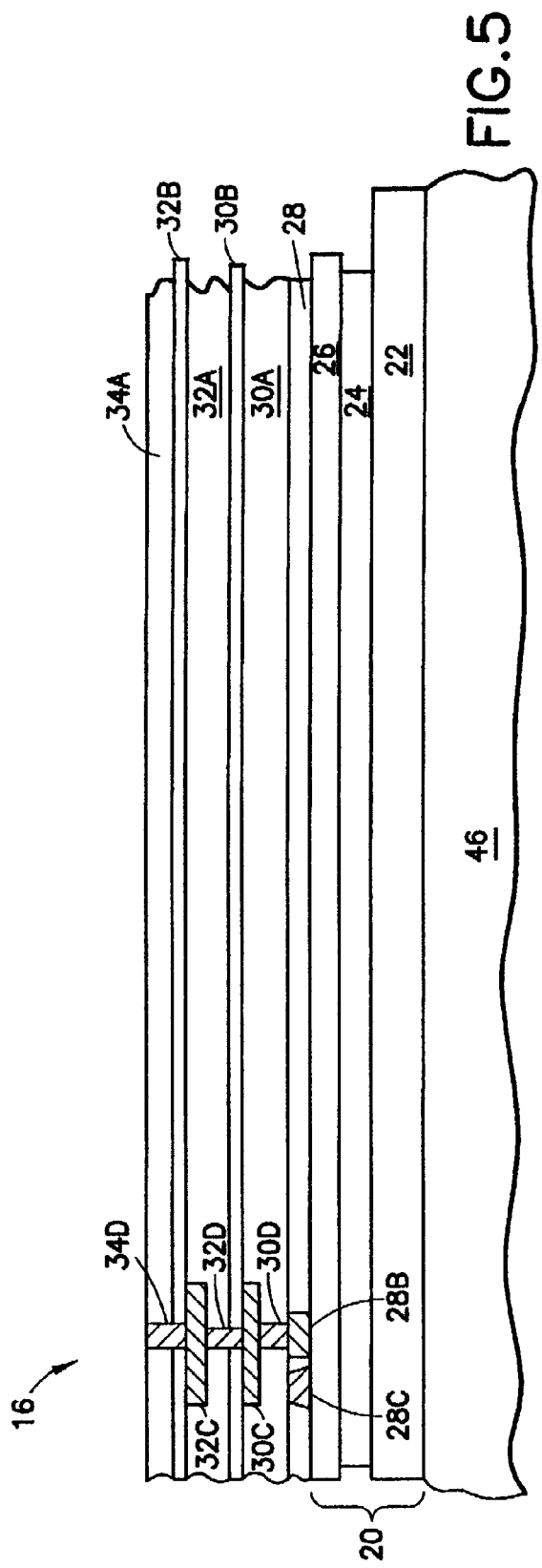
Figure 6:
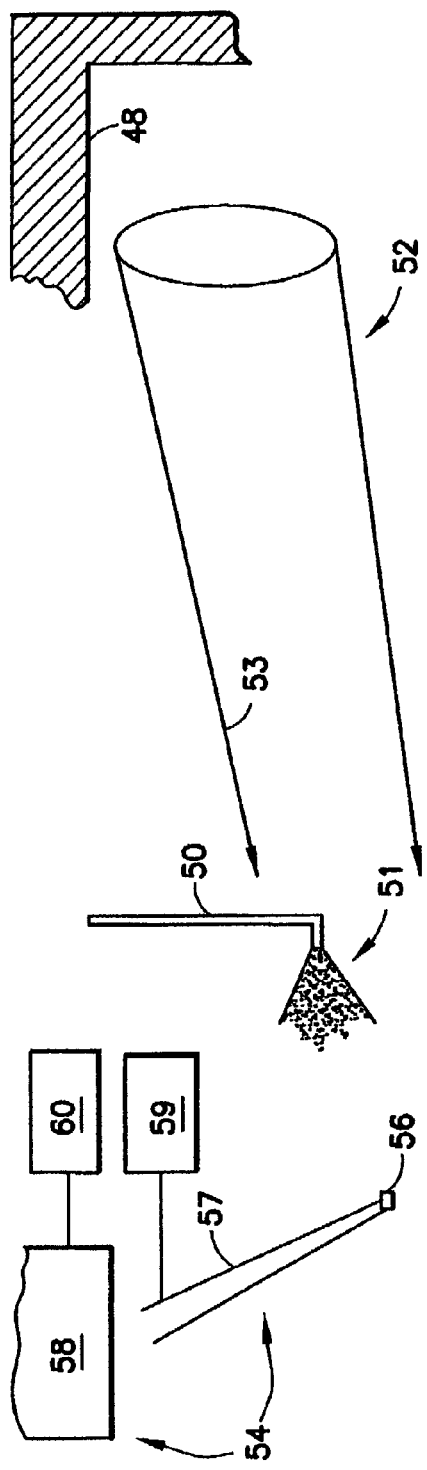
Figure 6:
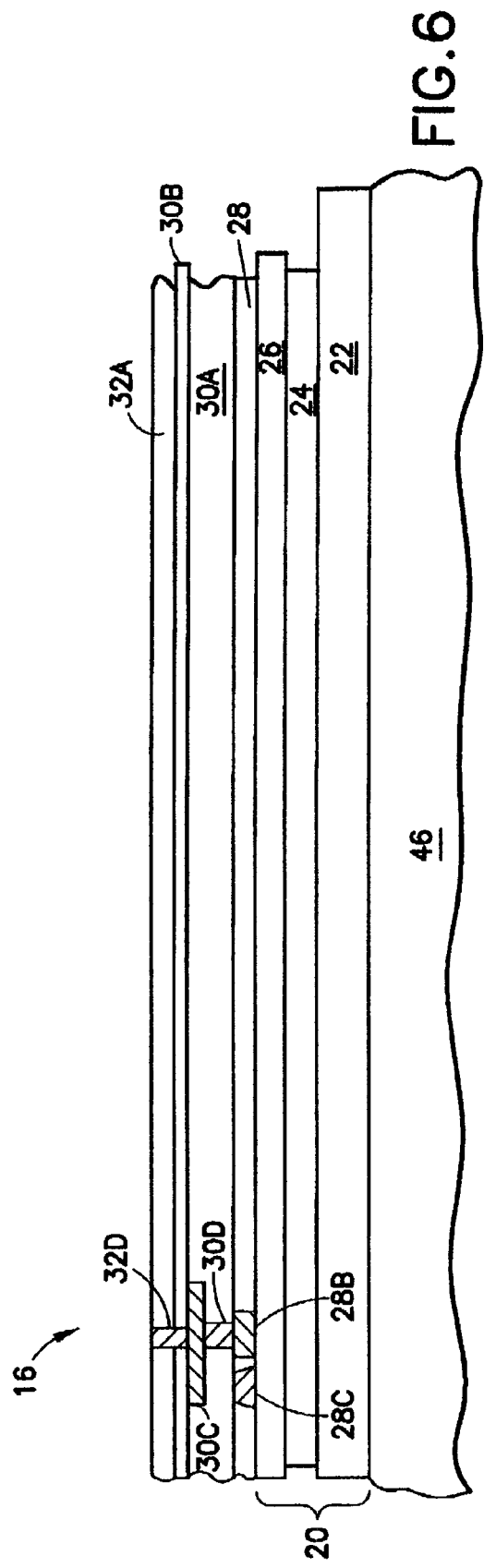

With reference now to FIGS. 5 and 6, structure 16 is shown with the above-described process steps repeated to expose low-k dielectric layers 34A (FIG. 5) and 32A (FIG. 6), respectively. The etching processes used to remove the intermediate nitride layers and copper metallurgy are substantially identical to those described above. Endpoint detector 56 and platen 46 are repositioned intermediate each etching step, in the manner described above, to optimize both the etching process and the endpoint detection.

Figure 7:
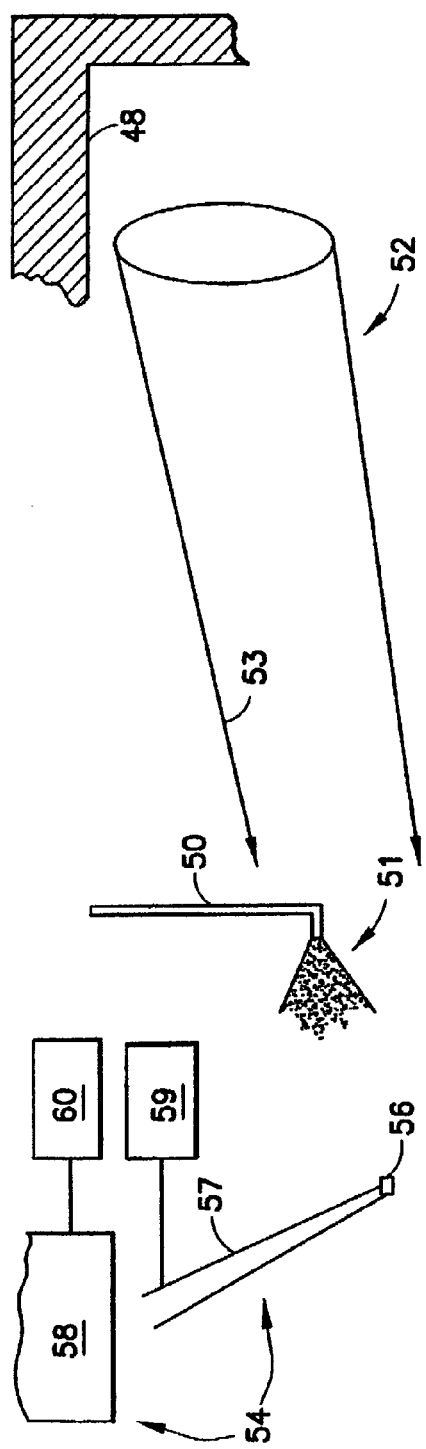
Figure 7:
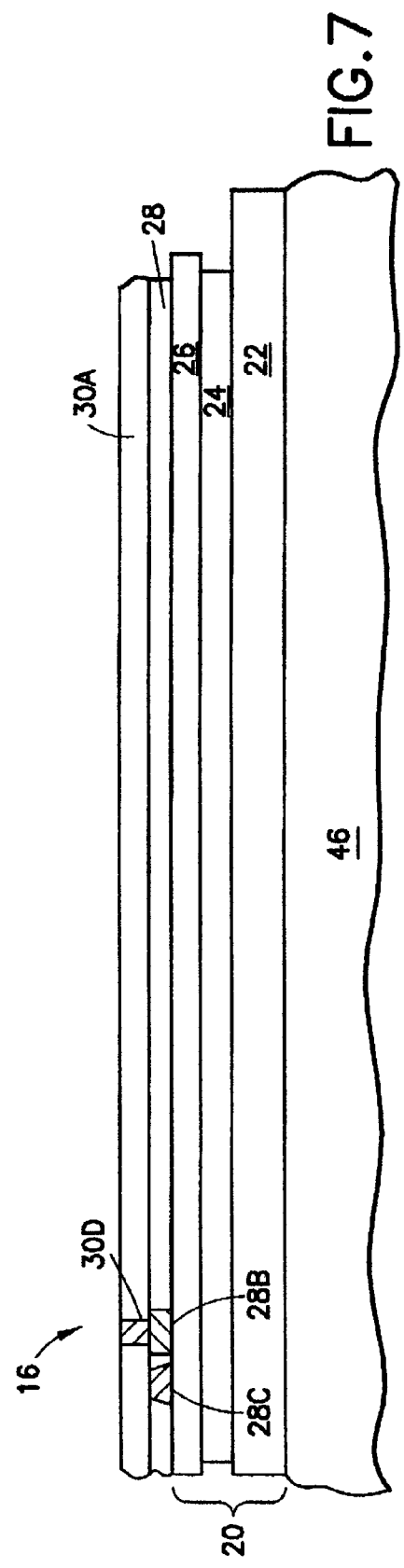

With reference now to FIG. 7, semiconductor structure 16 is shown with all of back-end structure 18 removed excepting a remaining portion of layer 30A overlying layer 28A, and the associated metallurgy 30D, 28B and FET gate 28C.

Methodology for Unlayering/Reworking Individual Die and Wafer Fragments with Low-K Dielectric Films Using Mechanical Polish/Removal of Metal/Metal Interconnects Combined with RIE or Plasma Deprocessing Steps:

The following methods allow for unlayering/deprocessing of Low-K spun-on dielectric films where each low k dielectric level has been built (ie. Hardmask, CMP endstop layer is intact) before unlayering/deprocessing is initiated.

Method (a)

Using a RIE etch (ie. CF4 process gas) or wet etch, remove nitride cap layer and hardmask (ie. Applied Materials BLOK™). Next remove spun-on Low-K Dielectric with Oxygen Plasma. Next deposit an oxide or tetraothrosilicate (TEOS) CVD layer to permit mechanical polish removal of metal/metal interconnection through the underlying SiLK layer to the hardmask or cap nitride layer. Next, deposit replacement cap layer. Resume normal spun on low k Dielectric film deposition.

Method (b)

Using a RIE etch (ie.CF4 process gas) or wet etch, remove nitride cap and hard mask (ie. Applied Materials BLOK™). Partially remove spun on low-K Film to top level of metal interconnection. Deposit oxide or CVD tetraorthosilicate insulator film in gap formerly occupied by low k spun-on dielectric film. Mechanically polish/remove via level/metal interconnection and metal level itself. Deposit CVD nitride cap layer. Resume normal spun-on low k dielectric film (ie. Dow Corning SiLK) film deposition.

Method (c)

Mechanically polish to remove the nitride cap and hardmask layer overlying metal and low-K spun on dielectric film. Remove spun-on low K dielectric film with oxygen plasma process. Deposit oxide layer or CVD tetraorthosilicate (TEOS) dielectric film in the gap formerly occupied by spun-on Low-k dielectric film. Mechanically polish to remove metal level along with deposited oxide/TEOS layer through underlying nitride cap and stop on hardmask. Deposit new CVD nitride cap layer. Resume normal spun-on low k dielectric film (ie. Dow Corning SiLK) deposition.

Method (d)

Mechanically polish to remove nitride cap and hardmask layer overlying metal and low-K spun on dielectric film. Partially remove spun-on low K dielectric film with oxygen plasma process to top of metal interconnection level. Deposit oxide layer or CVD tetraorthosilicate (TEOS) dielectric film in gap formerly occupied by spun-on Low-k dielectric film. Mechanically polish/remove metal level lines along with deposited oxide/TEOS layer. Deposit new CVD nitride cap layer. Resume normal spun-on low k dielectric film (ie. Dow Corning SiLK) deposition.

Method (e)

Use RIE (ie. CF4 process gas) or wet etch to remove nitride cap and hardmask layer (ie. BLOK ™). Alternatively, mechanically polish to remove nitride cap layer and hardmask layer (ie. BLOK™). Immerse sample in copper wet etch bath in order to remove metal and metal interconnection levels. Next, wet etch barrier liner (ie. Ta/TaN) material. Next, Plasma etch with oxygen process gas to remove low-k spun on dielectric film. Mechanically polish/remove residual metal interconnection layer and stop at hardmask material. Deposit replacement nitride cap layer. Resume normal spun-on low k dielectric film (ie. Dow Corning SiLK) deposition. Complete BEOL build cycle.

Method (f)

Use RIE (ie. CF4 process gas) or wet etch to remove nitride cap and hardmask layer (ie. BLOK ™). Alternatively, mechanical polish removal of the cap nitride and hardmask could be substituted, instead. First, expose wafer to a slow copper etchant to controllably remove the copper metal wiring levels and copper interconnection without etching into the underlying copper metal lands. Once the copper lands and copper interconnection levels are etched away (using a timed etch process), employ a different chemical etchant to remove the barrier liner metallurgy (typically a tantalum/tantalum nitride material) without attacking the underlying copper metal wiring. Next, perform an oxygen plasma etch to remove the spun on low-k dielectric film (ie. Dow Corning SiLK film) which will selectively stop on the underlying silicon nitride cap layer. Mechanically polish off the cap nitride along with any residual copper metallurgy and tantalum/tantalum nitride liner material. Redeposit CVD nitride cap layer. Resume normal spun-on low k dielectric film (ie. Dow Corning SiLK) deposition. Complete BEOL build cycle.

There have thus been described systems and methods using ion beam etching with endpoint detection for selectively etching multi-layer structures on semiconductor devices. The systems and methods of the present invention enable highly selective and controllable planar removal of different types of materials, including oxides, nitrides, metals and low-k dielectrics such as SiLK. They further permit such removal without damaging the soft, fragile, low-k dielectric materials. There have further been a set of processes for deprocessing spun-on low-k structures with copper metallurgy/copper interconnections.

The present invention can be used to facilitate, for example, the reworking and/or evaluation of semiconductor devices, particularly those incorporating low-k dielectric films. The invention thus has application in the manufacture, rework and analysis of semiconductor devices.

What is claimed is:

1. A method of etching a semiconductor structure including a first layer of material overlaying a second layer of low-k dielectric film, comprising the steps of:
   ion beam-milling said first layer of material; and
   detecting, with an optical detector positioned in the ion beam adjacent said first layer of material, an endpoint of said first layer;
   whereby to expose said second layer of low-k dielectric film.

2. A method in accordance with claim 1 wherein said first layer is selected from the group consisting of oxide, nitride, and metal.

3. A method in accordance with claim 1 wherein said detecting step comprises transmitting detected light through an optical cable to a photospectrometer.

4. A method in accordance with claim 1 and further including the steps of:
   supporting said semiconductor structure on a liquid-cooled, movable platen; and
   varying the temperature and position of said platen to facilitate said ion beam-milling step.

5. A method in accordance with claim 1 wherein said step of detecting an endpoint includes detecting the presence of said second layer of low-k dielectric film.

6. A method in accordance with claim 1, wherein said semiconductor structure includes a third layer of material underlying said second layer of low-k dielectric film; and further including the steps of:
   ion beam-milling said second layer of low-k dielectric film with Argon beams; and
   detecting, with an optical detector position in the ion beam adjacent said second layer of material, an endpoint of said first layer.

7. A method in accordance with claim 1 wherein said first layer of material is ion beam-milled using an inert noble gas.

8. A method in accordance with claim 7 wherein said inert noble gas is selected from the group consisting of argon, helium, neon, xenon and radon.

* * * * *